United States Patent [19]

Sacks

[11] Patent Number: 4,758,237
[45] Date of Patent: Jul. 19, 1988

[54] DEVICE FOR APPLYING LIQUID TO THE CORNEAL SURFACE OF THE EYE

[76] Inventor: Herman Sacks, 509 Skyline Lake Dr., Ringwood, N.J. 07456

[21] Appl. No.: 5,148

[22] Filed: Jan. 20, 1987

[51] Int. Cl.$^4$ .............................................. A61M 35/00
[52] U.S. Cl. .................................... 604/294; 604/297; 4/625
[58] Field of Search ...................... 433/81; 4/616, 619, 4/620, 621, 624, 625, 626, 630, 611; 604/28, 294–298, 300–302, 150; 239/16, 124, 332, 289, DIG. 23

[56] References Cited

U.S. PATENT DOCUMENTS

| | | | |
|---|---|---|---|
| 2,482,960 | 9/1949 | Benson | 604/294 |
| 3,925,829 | 12/1975 | Bost | 4/620 |
| 4,641,384 | 2/1987 | Landsberger et al. | 604/295 |
| 4,650,461 | 3/1987 | Woods | 604/28 |

*Primary Examiner*—C. Fred Rosenbaum
*Assistant Examiner*—J. L. Kruter
*Attorney, Agent, or Firm*—Ilya Zborovsky

[57] ABSTRACT

A device for applying a liquid to an eye has a liquid accommodating chamber with an opening limited by an edge so that the user's eye can be placed into contact with the edge with an eye surface facing toward the interior of the chamber, and a liquid circulating unit which forcedly circulates the liquid in the chamber to move the liquid in a direction which is transverse to an axis of the opening and along the eye surface.

11 Claims, 4 Drawing Sheets

DEVICE FOR APPLYING LIQUID TO THE CORNEAL SURFACE OF THE EYE

BACKGROUND OF THE INVENTION

The present invention relates to a device for applying a liquid to eyes, for example for removing foreign particles.

Devices of the above mentioned general type are known in the art. One of such devices is formed as an eye cup which is filled with a liquid and is used by placeing it onto a user's eye to apply the liquid (boric acid or similar eye washing solution) onto the eye. The disadvantage of this device is that the liquid is passively applied onto the eye and is not moved forcedly relative to the eye. Thereby the device is not very effective in washing the eyes. It is also known to wash eyes by a liquid coming from a fountain with liquid jets acting onto the eye perpendicularly to its surface. This action is very aggressive to the eye and nevertheless also does not effectively wash the eyes.

SUMMARY OF THE INVENTION

It is therefore an object of the present invention to provide a device for applying a liquid to an eye, which avoids the disadvantages of the prior art.

More particularly, it is an object of the present invention to provide such as device which performs a very gentle action upon an eye and at the same time effectively washes the eye, for example for removing foreign particles.

In keeping with these objects and with others which will become apparent hereinafter, one feature of the present invention resides, briefly stated, in a device for applying a liquid to an eye, which has a liquid accommodating chamber with an opening limited by an edge onto which an eye can be placed and the opening can be sealed, and circulating means arranged to circulate the liquid in the chamber so that the liquid is forcedly moved in a direction transverse to an axis of the opening and therefore along the eye surface.

When the device is designed in accordance with these features, the above objects of the present invention are fully achieved.

The novel features of the present invention are set forth in the appended claims. The invention itself is disclosed in the description of preferred embodiments which is accompanied by the following drawings.

DESCRIPTION OF A PREFERRED EMBODIMENT

Figure 1:
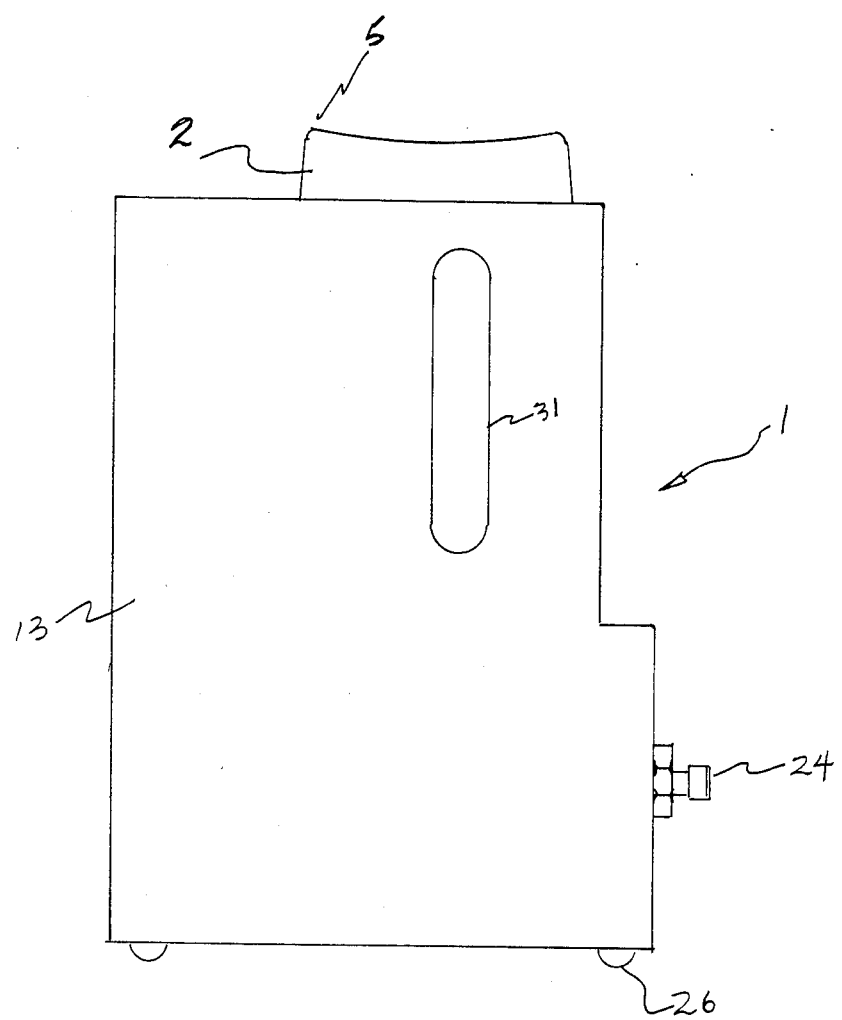
FIG. 1 is a front view of a device for applying a liquid to an eye in accordance with the present invention.
Figure 2:
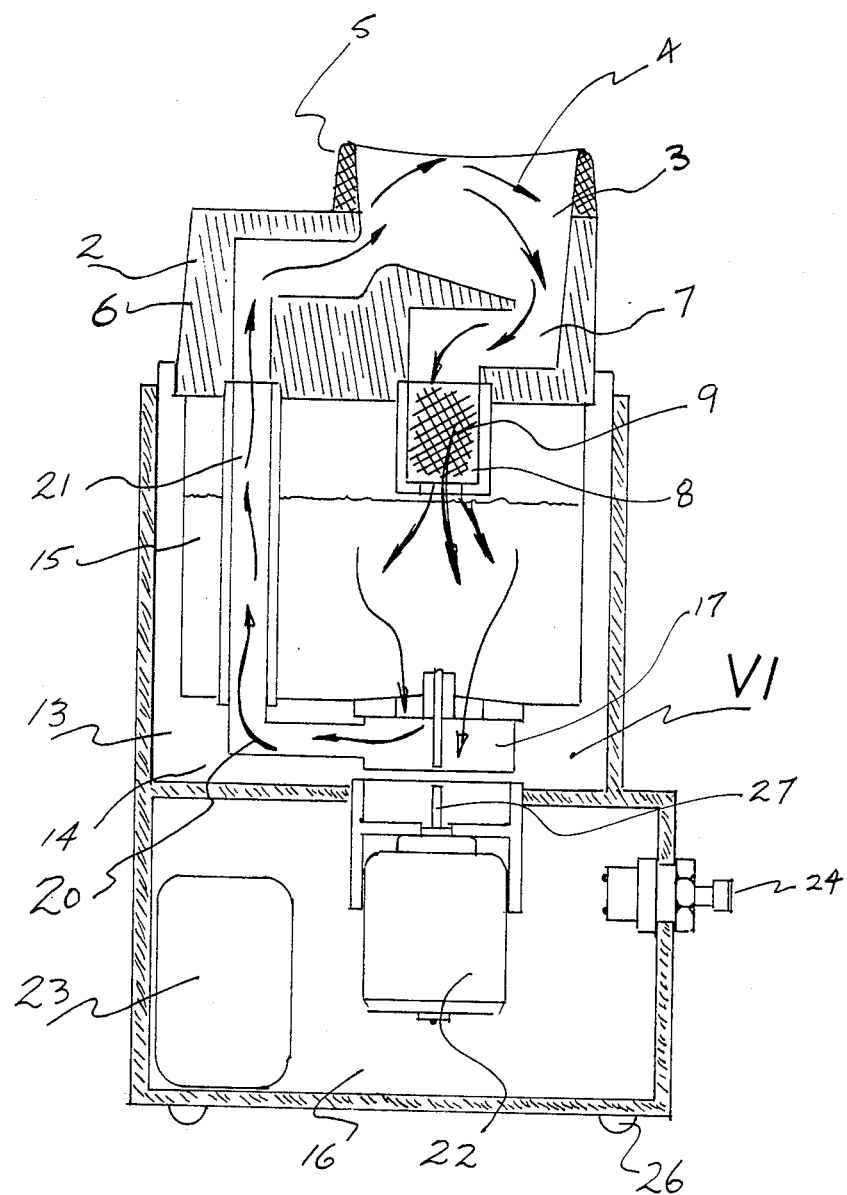
FIG. 2 is a cross section II—II of the device for applying a liquid, shown in FIG. 1.
Figure 3:
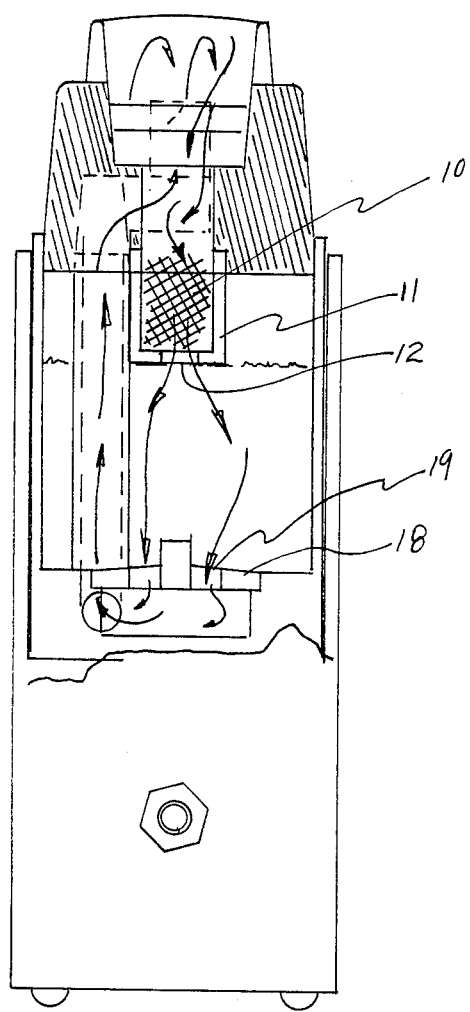
FIG. 3 is a side view of the device for applying a liquid, shown in FIG. 1, in section III—III.
Figure 4:
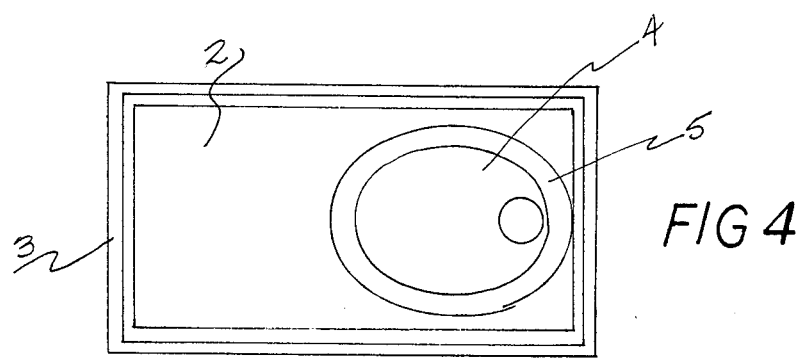
FIG. 4 is a plan view of the device for applying a liquid in accordance with the present invention.
Figure 5:
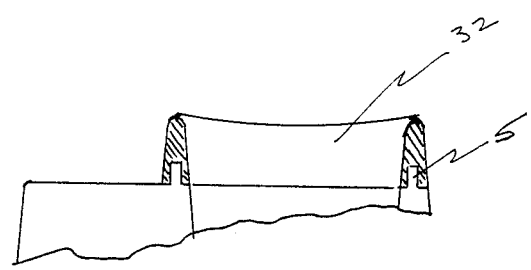
FIG. 5 is a view showing another embodiment of a liquid accommodating chamber and more particularly its opening limiting edge as seen in direction of arrow V.
Figure 6:
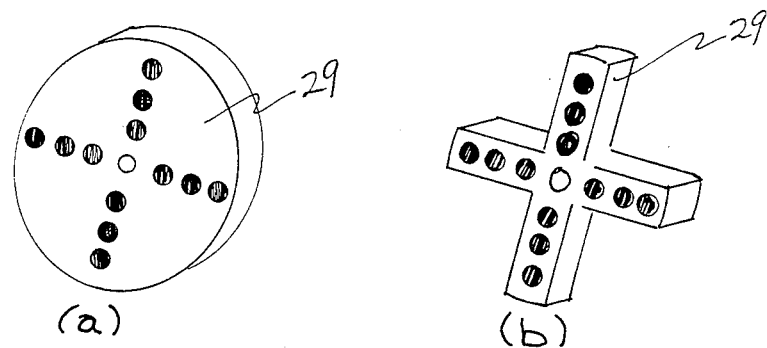
FIG. 6 is a view showing in detail a unit drive and impeller for circulating the liquid in the device in accordance with the present invention.
Figure 6:
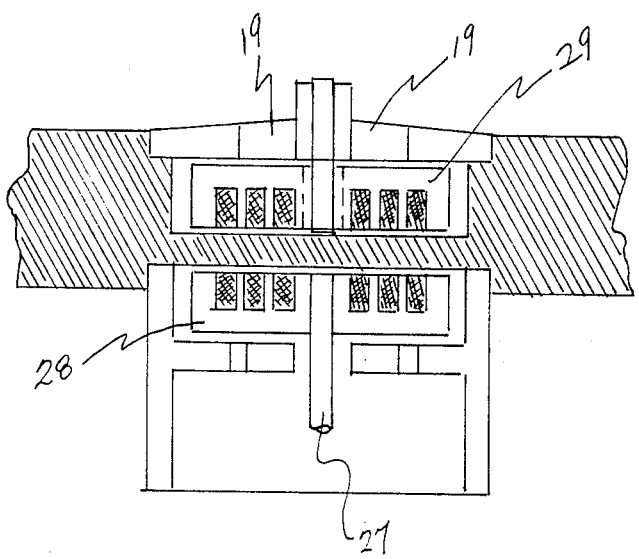

A device for applying liquid to an eye 1 has an upper body 2 which forms a liquid accommodating chamber 3. The chamber 3 has an opening 4 which is limited by a projecting edge 5. The upper body 1 has a supply passage 6 and a withdrawal passage 7 for supplying liquid into the chamber 3 and withdrawing the liquid from the same after use. A filter 8 is arranged in the withdrawal passage 7, preferably removably. The filter 8 includes for example a filtering material 9, such as Dacron, which is arranged in an inner chamber 10 of a filter casing 11. The latter is provided with an outlet opening 12.

The device further has a lower body 13 which is subdivided by a partition 14 into a liquid reservoir 15 and a motor compartment 16. The upper and lower bodies 2 and 13 are removably connectable with one another, for example by snap action. The liquid reservoir 15 is to be filled with a body of liquid, for example eye washing liquid. A pump chamber 17 is formed in the bottom of the reservoir 15 or the partition 14 and is closed from above by a plate 18 provided with inlet openings 19. A supply passage 20 extends from the pump chamber 17 and communicates with the supply passage 6 of the upper body 2 through a pipe 21.

The motor compartment 16 accommodates an electric motor 22 which is power supplied from a battery 23 and actuatable by a switch 24. The motor compartment 16 is closed from below by a cover 25 provided with legs 26 and removable for mounted purpose and exchange of the battery. The motor 22 carries on its shaft 27 a first magnetic member 28 which is provided with a plurality of magnetic segments. The pump chamber accommodates an impeller 29 which forms a second magnetic member and also has a plurality of magnetic segments. The magnetic members together form a magnetic coupling between the motor shaft 27 and impeller 29.

The device operates in the following manner:

A user places his or her eye onto the opening 4 of the liquid accommodating chamber 3 so that the tissues around the eye tightly abuts against the edge 5 and the eye surface faces toward the interior of the chamber. The electric motor 22 is turned on by the switch 24 so that the shaft 27 is rotated and rotates the magnetic member 28 which induces the rotation upon the magnetic member thus causing the impeller 29 to rotate in the pump chamber 17. The rotation of the impeller 29 causes suction of the liquid from the reservoir 15 through the openings 19 into the pump chamber 17, and then pumping the liquid through the passage 20, the pipe 21 and the passage 6 into the chamber 3. In the chamber 3 the liquid is forcedly moved in a direction from the supply passage 6 to the withdrawal passage 7 and transversely to the axis of the opening 4. In other words, it is forcedly moved along the eye surface from its one corner to its other corner, preferably from its outer corner toward the inner corner located near the user's nose. During this forced movement the liquid flushes off all particles from the user's eye. The liquid with the particles then flows through the filter 8 which retains the particles, while the clean liquid flows back into the reservoir 15.

The filter 8 can be periodically removed for cleaning or exchange. The battery 23 can be removed for replacement by a new battery or can be formed rechargeable. The lower body 13 can be provided for an observation window 31 for visual determination of a liquid level in the container 15. Finally, the edge 5 of the upper body 2 can be provided with a soft and elastic member 32 fitted on the edge for making the contact of the user's eye with the edge more comfortable and creating a better seal.

The liquid reservoir can be formed removable from the motor compartment for easy cleaning and refilling.

It is also possible, instead of returning the liquid into the reservoir, to withdraw it completely from the device after having been used.

The invention is not limited to the details shown, since various modifications and structural changers are possible without departing from the spirit of the invention.

What is desired to be protected by Letters Patent is set forth in the appended claims:

1. A device for applying liquid to an eye, comprising means forming a liquid accommodating chamber, said liquid accommodating chamber having an opening having a peripheral seal means into which an eye ball is placed which further has a vertical axis, said liquid accommodating chamber also having an edge means which limits the size of said opening, so that when a user places the eye on said periperal seal means said opening is sealed from outside and the eye corneal surface faces and extends toward the interior of said chamber;

means forcedly circulating a liquid through said chamber in a direction transverse to said axis of said opening, so that when the user's eye is placed on said edge the liquid is forcedly moved by said circulating means horizontally along the eye corneal surface of the eye;

means forming a liquid reservoir, said circulating means being formed to supply the liquid from said liquid resevoir into said liquid accommodating chamber and to withdraw the liquid from said liquid accommodating chamber to said reservoir after having been applied to the eye, said circulating means including an electric motor, an electric battery connected with the latter to provide power supply, and an impeller rotatable by said electric motor in said liquid reservoir.

2. A device for applying liquid to an eye as defined in claim 1, wherein said opening of said liquid accommodating chamber is elongated in an elongation direction, said circulating means being formed so that the liquid is forcedly moved by said circulating means in said accommodating chamber in said elongation direction, so that when the user's eye is placed on said edge the liquid is forcedly moved along the eye surface in direction from one eye corner to the other eye corner.

3. A device for applying liquid to an eye as defined in claim 1, wherein said means forming a liquid accommodating chamber is removably attachable to said liquid reservoir forming means so as to expose said liquid reservoir for refilling the same with the liquid.

4. A device for applying liquid to an eye as defined in claim 1; and further comprising means forming a motor compartment located adjacent to said liquid reservoir and liquid-tightly separated therefrom, said electric motor and said electric battery being located in said motor compartment.

5. A device for applying a liquid to an eye as defined in claim 4; and further comprising a parition separating said motor compartment from said liquid reservoir, said electric motor being provided with a first magnetic member rotatable by said motor and located in said motor compartment, said impeller being provided with a second magnetic member located in said liquid reservoir and inducable in rotation together with said impeller by said first magnetic member through said partition.

6. A device for applying a liquid: to an eye as defined in claim 5, wherein said electric motor has a rotatable shaft, said first magnetic member being mounted on said shaft and including a plurality of magnetic segments, said second magnetic member being fixedly connected with said impeller and also including a plurality of magnetic segments.

7. A device for applying liquid to an eye as defined in claim 1; and further comprising means for filtering the liquid after its use in said liquid accommodating chamber and before entering said liquid reservoir.

8. A device for applying liquid to an eye as defined in claim 7, wherein said circulating means includes a withdrawing passage communicating said liquid accommodating chamber with said liquid reservoir and arranged for withdrawing the liquid after use from the former to the latter, said filtering means including a filter element arranged in said withdrawing passage.

9. A device for applying liquid to an eye as defined in claim 8, wherein said filter element is removably attached to said means forming a liquid accommodating chamber.

10. A device for applying a liquid to an eye as defined in claim 1, wherein said liquid reservoir forming means is provide with an observation window for determining visually a liquid level in said container.

11. A device for applying a liquid to an eye as defined in claim 1; and further comprising means for softening a contact of the user's eye with said edge and including a substantially soft member fittable on said edge.

* * * * *